United States Patent [19]

Falk

[11] Patent Number: 5,168,764
[45] Date of Patent: Dec. 8, 1992

[54] METHOD AND APPARATUS FOR TAKING METAL SAMPLES

[76] Inventor: Richard A. Falk, 1081 Hillsboro Mile A1A, Hillsboro Beach, Fla. 33062

[21] Appl. No.: 559,228

[22] Filed: Jul. 23, 1990

[51] Int. Cl.$^5$ .............................................. G01N 1/12
[52] U.S. Cl. .................................. 73/864.59; 73/866.5
[58] Field of Search ........................ 73/866.5, DIG. 9, 864.51–864.59, 73/865.5; 374/139, 140; 266/99, 100

[56] References Cited

U.S. PATENT DOCUMENTS

| | | | |
|---|---|---|---|
| 3,374,122 | 3/1968 | Cole | 374/140 |
| 3,390,578 | 7/1968 | Moore | 374/140 |
| 3,396,580 | 8/1968 | Cole | 374/140 |
| 3,463,005 | 8/1969 | Hanle | 374/140 |
| 3,577,886 | 5/1971 | Wiese | 374/139 |
| 3,597,975 | 8/1971 | Kern et al. | 374/140 |
| 3,673,869 | 7/1972 | Stawarski et al. | 374/140 |
| 3,717,034 | 2/1973 | Dukelow et al. | |
| 4,964,736 | 10/1990 | Lure et al. | 374/139 |

FOREIGN PATENT DOCUMENTS

1008231 10/1965 United Kingdom ................ 374/139

*Primary Examiner*—Robert Raevis
*Attorney, Agent, or Firm*—Fuller, Ryan & Hohenfeldt

[57] ABSTRACT

A method and apparatus for storing and releasing individual probes from a drop mechanism or probe rack which stores a number of these probes in a ready position for future use. The probe rack includes a plurality of radially projecting pins which are connected to, or comprise the piston rods of, a plurality of radially extending air cylinders. The individual probes are each provided with hanger loops which are suspended on the support pins in a ready position. Each of the probes may have a thermocouple assembly, or an oxygen sensor, or some other type of sensor. When it is desired to drop or release one of the probes, a switch is closed on a remotely located control panel to energize the appropriate air cylinders to withdraw the pin from the probe loop and allow the selected probe to drop into the additive chute of the vessel. The descent of the probe into the chute and through the chute into the molten metal bath is guided by the electric cable which has wires to connect the sensor to the instrumentation involved. The method includes dropping the probe so that an elongated pipe intermediate the length of the probe penetrates the slag and receives a skull of steel which adds to the weight of the second weight to add in maintaining the probe in an upright position.

6 Claims, 6 Drawing Sheets

METHOD AND APPARATUS FOR TAKING METAL SAMPLES

FIELD OF THE INVENTION

The invention relates to molten metal sampling apparatus for taking measurements in a molten metal bath.

BACKGROUND OF THE INVENTION

In the basic oxygen process for making steel, the furnace typically includes a tiltable vessel. A hood is located over the open top or mouth of the vessel for conveying fumes and smoke to a waste collection and purification chamber. Various devices have been involved for accessing the interior of the furnace to take oxygen readings and temperature measurements without turning the vessel partially on its side. U.S. Pat. No. 3,717,034 discloses a sublance arrangement which enables insertion and retraction of sampling equipment with a permanent installation. These types of sublances are very expensive and cost several million dollars to install. Moreover, they take considerable time to use increasing the time of completing a "heat".

Typically the water cooled hood for the furnace is provided with a chute leading into the furnace for introducing various additives which may be required during the steel making process. The chute enables access to the interior of the vessel. Measuring devices are available which involve the use of expendable thermocouples which are weighted and supported only by an electrical cord. After use the thermocouple unit and cord are consumed by the high temperature bath. U.S. Pat. No. 3,374,122 is an example of an expendable sensor which is lowered through the chute into a metal bath. The disclosure in U.S. Pat. No. 4,881,824, of which applicant is a co-inventor, provides an improved expendable probe. The present invention provides apparatus for convenient use of this probe with the operator located at the furnace control station at the pulpit.

SUMMARY OF THE INVENTION

The invention provides a method and apparatus for storing and releasing individual probes from a drop mechanism or probe rack which stores a number of these probes in a ready position for future use. The probe rack includes a plurality of radially projecting pins which are connected to, or comprise the piston rods of, a plurality of radially extending air cylinders. The individual probes are each provided with hanger loops which are suspended on the support pins in a ready position. Each of the probes may have a thermocouple assembly, or an oxygen sensor, or some other type of sensor. When it is desired to drop or release one of the probes, a switch is closed on a remotely located control panel to energize the appropriate air cylinders to withdraw the pin from the probe loop and allow the selected probe to drop into the additive chute of the vessel. The descent of the probe into the chute and through the chute into the molten metal bath is followed by the electric cable which has wires to connect the sensor to the instrumentation involved.

The electric cables for each probe are packed in separate canisters. The canisters are supported by a radially extending fixed pin on the probe rack which extends through loops fixed to the canisters. The length of cable needed to allow the probe to reach the molten metal is packed into the interior of the canister. When the probe is released the weight of the probe will withdraw the packed cable from the interior of the canister. The canisters are readily mounted to the probe rack and the electrical connections for each probe are made by simply plugging the free end of the cable into electrical outlets arranged around the probe rack.

The release of the probes from the probe rack can be controlled either from the drop rack itself or from the pulpit. The control panel at each location is provided with indicator lights, such as light emitting diodes, to indicate which probes are ready and that a probe has been released.

It has been found that it is desirable to adhere a layer or skull of steel on the elongated pipe weight which is exposed between the float and the lower weight. The added weight helps hold the probe submerged in the melt at the desired depth for accurate readings. The steel skull is acquired by dropping the probe in a free fall from a sufficient height to momentarily penetrate the steel below the slag before the buoyant forces buoy the pipe above the slag-steel interface into an equilibrium position.

Further objects, advantages and features of the invention will become apparent from the disclosure.

DESCRIPTION OF A PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Figure 1:
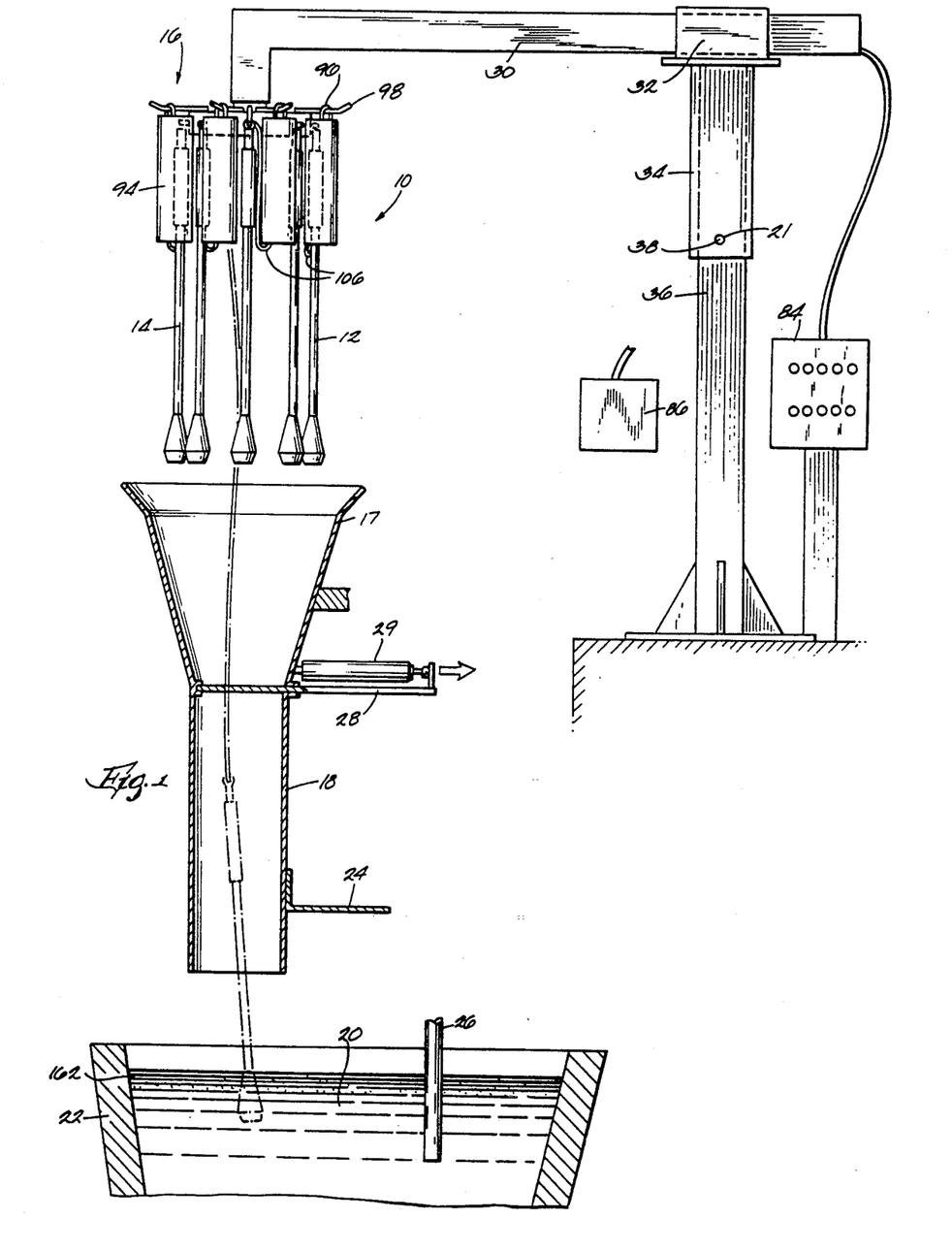
FIG. 1 is a diagrammatic view of the probe drop apparatus of the invention.

In the drawings, FIG. 1 discloses probe drop apparatus 10 with the individual probes 12 and 14 supported by a probe rack 16. The probes 12 and 14 can be provided with sensors such as thermocouples or oxygen sensors in accordance with U.S. Pat. No. 4,881,824, the entire disclosure of which is incorporated herein by reference.

The probes are positioned over an access hole to the chute 17 which is typically employed to add steel making ingredients through the conduit 18 into the metal bath 20 contained by a vessel 22. Conduit 18 and chute 17 are supported conventionally on the hood 24 of the steel making vessel 22. An oxygen blowing probe 26 is also shown in FIG. 1.

In accordance with the invention, the chute 17 is provided with a gate valve 28 operated by power cylinder 29 to seal the chute to prevent toxic gases or corrosive gases from deteriorating the drop rack and components thereof.

The probe rack 16 is supported on an adjustable boom arm 30 which is adjustably received in a sleeve 32, which is in turn rotatably supported by a sleeve 34 on a support post 36. Sleeve 34 can be pinned by a pin 38 receivable in any of a plurality of apertures 21 in post 36 in the appropriate angular position to register the probe rack with the chute 17.

Figures 2, 3:
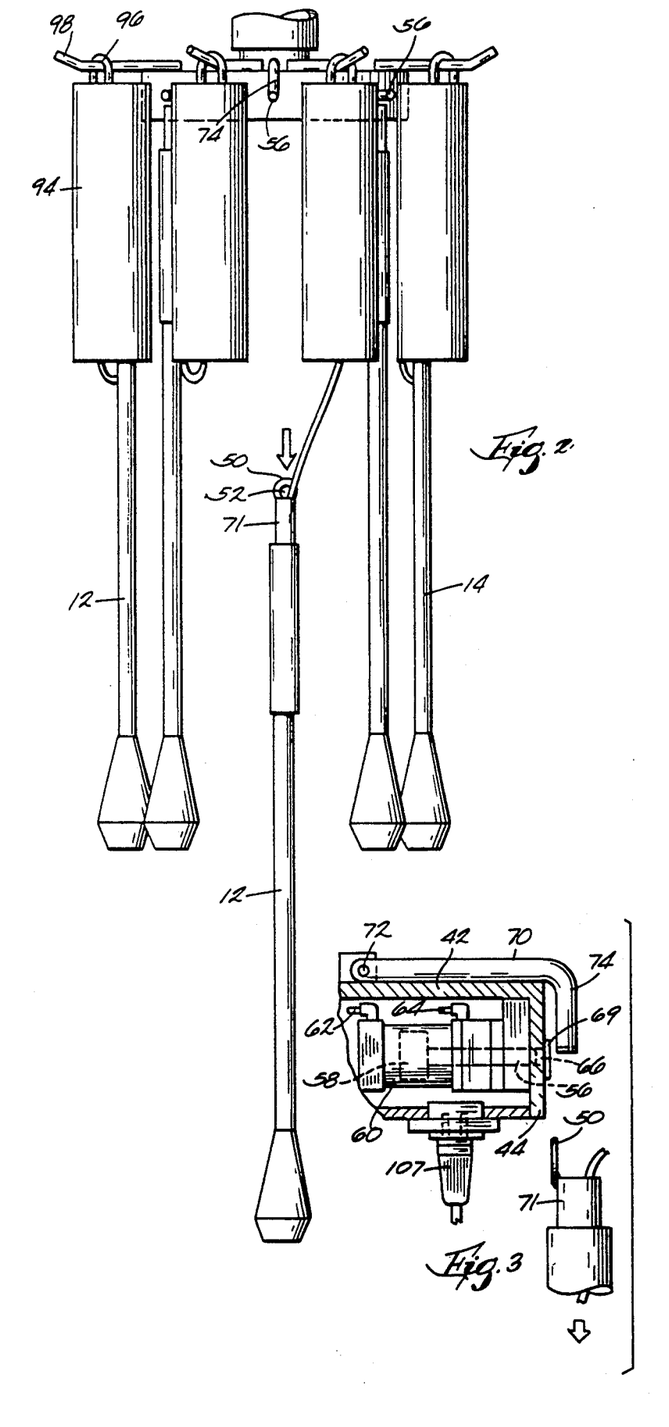
FIG. 2 is an enlarged view of the probe drop apparatus shown in FIG. 1.
FIG. 3 is a diagrammatic view showing the release of a probe from the probe rack.
Figure 4:
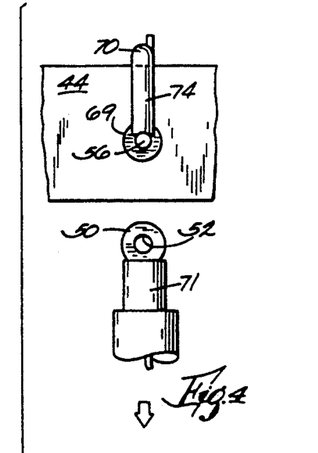
FIG. 4 is a view similar to FIG. 3 but a side view.
Figure 5:
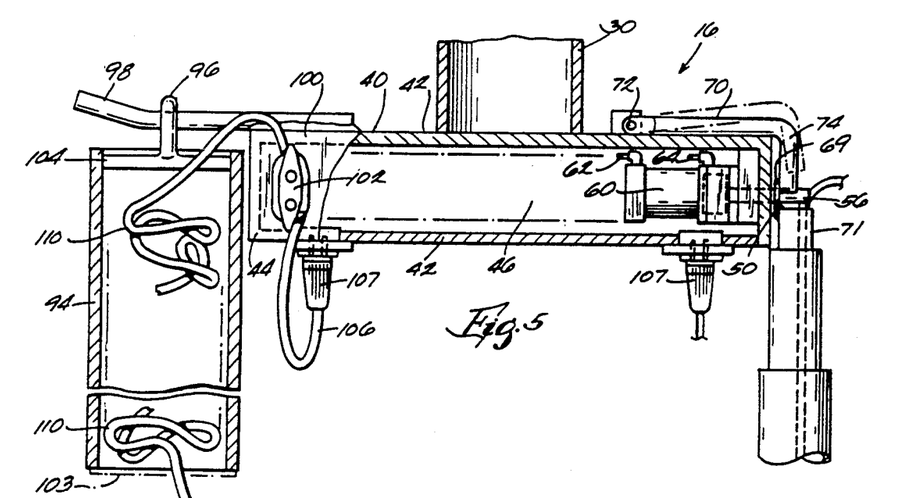
FIG. 5 is an enlarged view in partial section of the probe drop apparatus.
Figure 6:
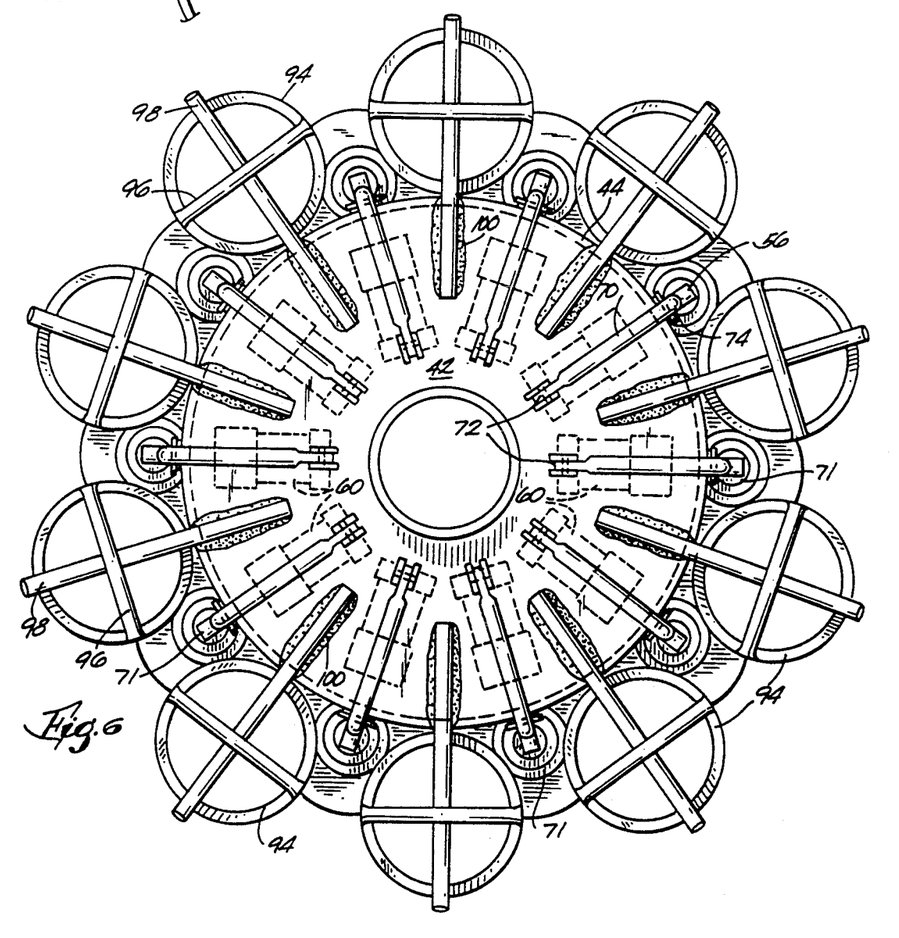
FIG. 6 is a plan view of the probe drop apparatus.

Means are provided for supporting and releasing the probes 12 and 14. As shown in FIG. 5, the means comprises a probe drop rack or a boom head 16 connected to the .boom 30. Boom head 16 includes two spaced walls 40 and 42 connected by a cylindrical peripheral wall 44 to define a chamber 46 which contains and supports elements of the drop mechanism. The probes 12 and 14 are provided with an eye 50 with an aperture 52 (FIGS. 3, 4). The eye 50 is secured in the end of the probe 12. The apertures 52 interfit with retractable pins 56 on the drop rack 16. As shown in FIG. 5, 6 the pins 56 are connected to the piston 58 of an air cylinder 60. The air cylinder is provided with inlet and outlet ports 62, 64 to either advance the pins 56 to the advanced position shown in FIG. 5 to support the probes 12, 14 in a really position, or retract the pins 56 to the retracted position shown in FIG. 3 when the probe is released. The pins 56 extend through apertures 66 in the cylindrical side wall 44 and through washers. or bearing surfaces 69. The eyes 50 are offset from pipe end 71 as shown in FIG. 5.

Figure 9:
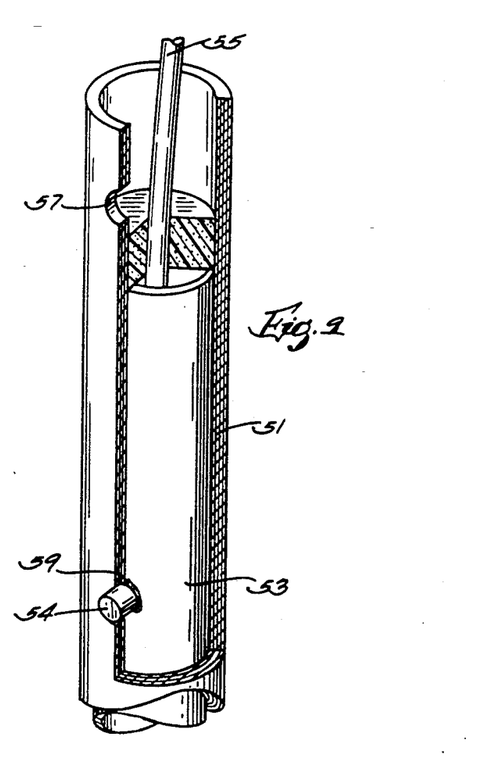
FIG. 9 discloses a fragmentary perspective view of a modified embodiment of the probe in fragmentary section.
Figure 10:
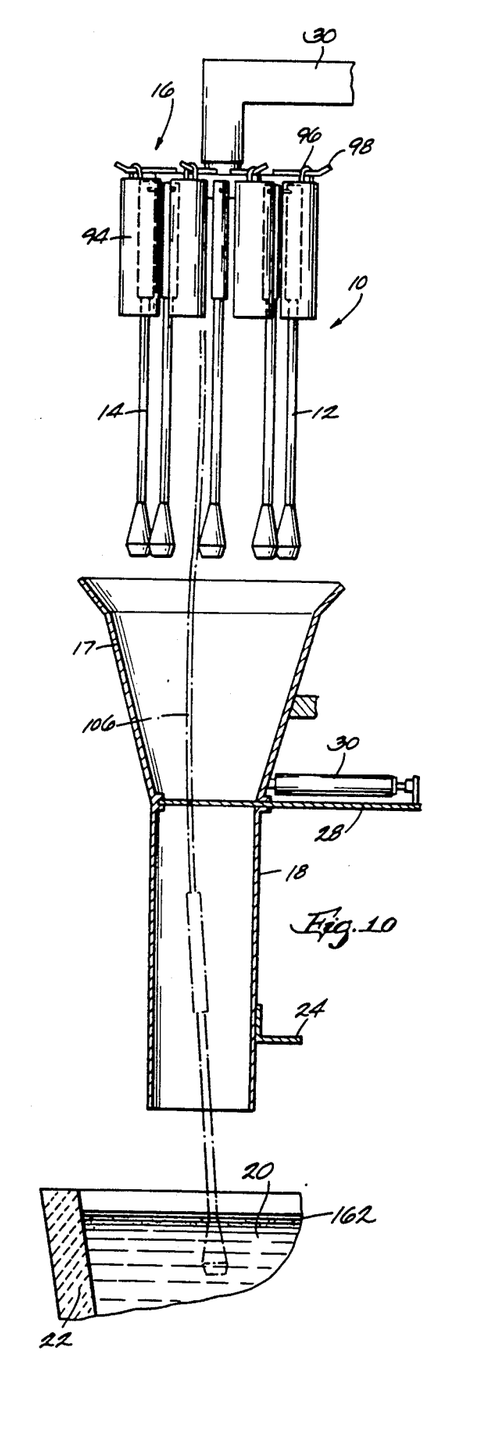
FIG. 10 is a view of the probe in FIG. 9 supported on the rack.
Figure 11:
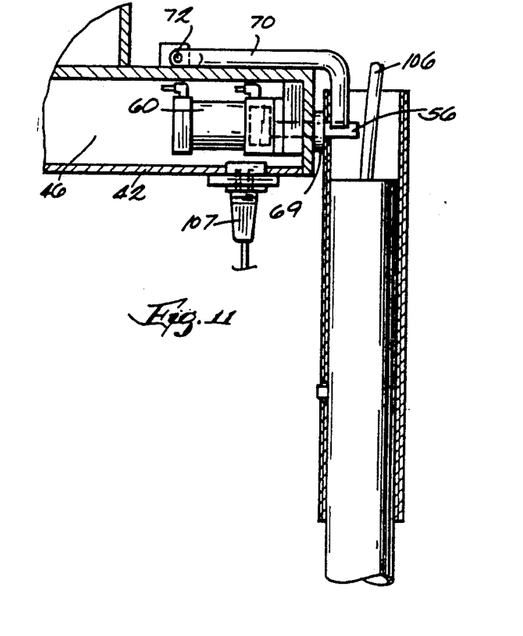
FIG. 11 is an enlarged fragmentary view of the connection of the probe to the rack of the FIG. 9 probe.

FIGS. 9, 10 and 11 show a modified embodiment of a probe in which a paperboard sleeve or float tube 51 is arranged over the end of a pipe 53 which extends to or is connected to the head containing sensor's or a sampler. A wire 55 extends through the sleeve 51 and pipe 53 to electrically connect the sensor head with instrumentation. An aperture 59 is provided in the side wall of sleeve 51 to receive a pin or plug 52 welded to the pipe 53. An aperture 57 is provided to receive pin 56 to support the probe on drop rack 16. The use of the paperboard aperture 57 rather than the eye 50 reduces the likelihood that the wire 106 will be burned off when the probe is dropped in the bath thus breaking the circuit before a reading is obtained with the sensor. Eye 50 and exposed pipe end 71 in FIG. 5 can cause slag to stick to these metal parts at the upper end of the probe with the concentration of hot metal burning through the wire over a brief period of time.

Hold down arms 70 are pivotally connected at 72 to the top wall 40 and have a depending portion 74 which is aligned to engage the projecting pins 56. The arms 70 are manually placed in position when loading the rack and the depending portion 74 holds the eye in place on the pin 56 until the power cylinder 60 is energized to retract the pin and release the probe 12 or 14.

Electric control means 84 are provided at the probe rack and also a remote control means 86 is provided for operation from the pulpit. The circuit includes indicator lights which indicate when a unit is ready to be dropped and that it has been dropped. When a probe is installed and plugged into the receptacle as hereinafter described on the drop rack, a light on both the upper control box and the pulpit drop control lights indicate that the unit is in place and that the thermocouple is good and operating.

Figure 7:
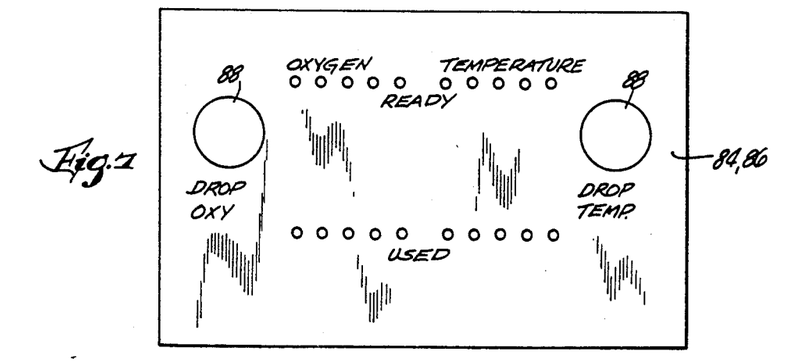
FIG. 7 is an example of a control panel which could be associated with a circuit constructed according to a preferred embodiment of the invention.

While any suitable control box could be used, FIG. 7 shows an example of such a control box as would appear both at the probe rack and at the pulpit. It would be advantageous to have the same control box at both locations so as to fully enable an operator in either position to perform all control functions. As shown in the example in FIG. 7, each control box 84, 86 may have one "Ready" light, such as a green light, and one "Used" light, such as a red light, for each probe. While the types of probes may be divided or allocated in any suitable way, the types of probes shown in the example in FIG. 7 are divided into two types, Oxygen probes and Temperature probes, with banks of indicator lights arranged to relate to each type. A separate "Drop" button 88 is provided for each type of probe.

Figure 8:
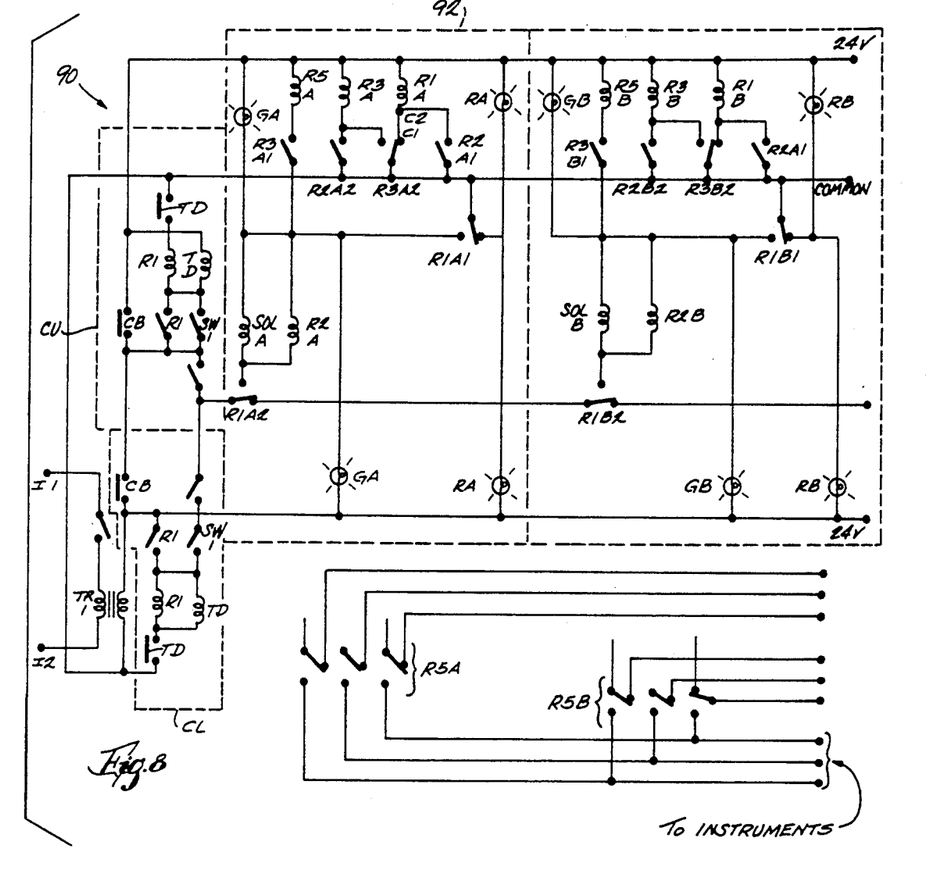
FIG. 8 is a schematic view of a control circuit constructed according to a preferred embodiment of the invention.

Shown in the schematic of FIG. 8 is a control circuit 90 constructed according to a preferred embodiment of the invention. According to the invention, as indicated above with respect to the control panel 84, 86 shown in FIG. 7, the circuit 90 includes two identical control units CU and CL, for the upper and lower control panels respectively, and one probe circuit 92 for each probe 12, 14. The probe circuits 92 are connected in series as shown in FIG. 8 to both control units CU, CL. Each of the control units CU, CL includes a normally open push button switch SW1 which corresponds to the drop button 88 for a particular type of probe a- indicated on the control panel 84, 86 of FIG. 7.

In accordance with the invention, means are provided for storing and releasing electric cable connected to the probes 12 and 14. In the disclosed construction of FIG. 5, the means includes canisters 94 which can be cylindrical in shape and which include a support eye 96 adapted to receive a radially projecting support hook 98 secured at 100 to the top wall 40a of the drop rack housing. The support loops 96 are secured to the top of the canister. Electric cable means 106 are wrapped around a cleat 102 to secure the wire to the rack. Cable means 106 terminates in a plug 107 which is plugged into- an electrical outlet 108 for connecting an electric circuit to the probe for the instrumentation associated with the probe. The cable length 110 which will extend from the drop rack into the molten metal is manually stuffed into the canister below the cross member 104. A paper or frangible bottom 103 can be employed to retain the cable in the canister until the probe is dropped. When the probe is released the weight of the probe will pull the cable loops from the canister as the probe heads toward the molten metal bath. The probes can be pre-wired to the canister assemblies so that the probe and cable canister are installed as a unit for replacement.

Referring now again to the control circuit 90 shown in FIG. 8, line power, such as at 110 volts, is supplied at power input terminals I1 and I2. This line voltage is stepped down to 24 volts at stepdown transformer TR1. When a probe 12, 14 is installed on the drop rack 16 and the plug 107 is plugged into the A outlet 108 or first probe outlet, the probe is electrically connected to the circuit 90. Since the probe has an internal closed circuit, this connecting action closes contacts Cl and C2 of the outlet 108. This in turn energizes relay R1A, switching contacts R1A1 and R1A2 from their normally closed contacts to their normally open contacts, thereby energizing the green indicator GA. Hence at the control panel 84, 86 the first green light GA will light up. The rest of the green lights will light up when probes are plugged into their respective outlets 108, indicating that the probes are attached and ready to be dropped.

In operation of the units, then, referring to FIGS. 7 and 8, pushing the drop button 88 on the control panel 84, 86 closes a switch SW1 (FIG. 8), which energizes a time delay relay coil TD besides energizing the coil of locking relay R1. Contacts TD remain open for a time, though contacts R1 close to maintain coil TD energized. At the same time, coil R2A is energized, as is the solenoid SOLA, in turn energizing the power cylinder which directly releases the probe from the rack. Coil R2A closes contacts R2A1 and R2A2. Contacts R2A1 maintain the green light GA on even though the closed circuit of the probe may open. Contacts R2A2 energizes coil R3A. In turn, coil R3A switches contacts R3A2 from the normally closed position at outlet contact Cl to the normally open position, so that R3A in effect locks itself in, remaining energized as long as its own contacts are closed. In addition, contacts R3A1 energize coil R5A. When this happens, contacts R5A, at the very bottom of the diagram, switch over to connecting the probe to be connected to sensing instruments so that the measurements, such as for temperature and oxygen, can register from the probe on the instruments. Thereafter, when the time delay relay TD times out, the green light GA is turned off and the red light RA is turned on.

In similar manner, each of the other probes 12, 14 is released, and each corresponding green light GB, etc. is turned off while the respective red light RB, etc. is turned on. Then, during reloading, the clear button CB is pushed so that the red lights RA, RB, etc. go out. The green lights GA, GB, etc. will then go on again when the new probes 12, 14 are plugged into the outlets 108.

As those skilled in the art will appreciate, the cords and probes can be attached together so that the drop of each probe 12, 14 pulls out the dangling cord 106 of the previously dropped probe, so that cord is consumed along with the current probe.

When the selected probe has been released by energizing the power cylinder to withdraw the pin 56, the probe will drop down the chute 16 through the pipe 18 into the molten metal bath. The probe and the wire 10 will be consumed after approximately 30 seconds. The canisters can be rewired with new wire assemblies and probes.

Figure 12:
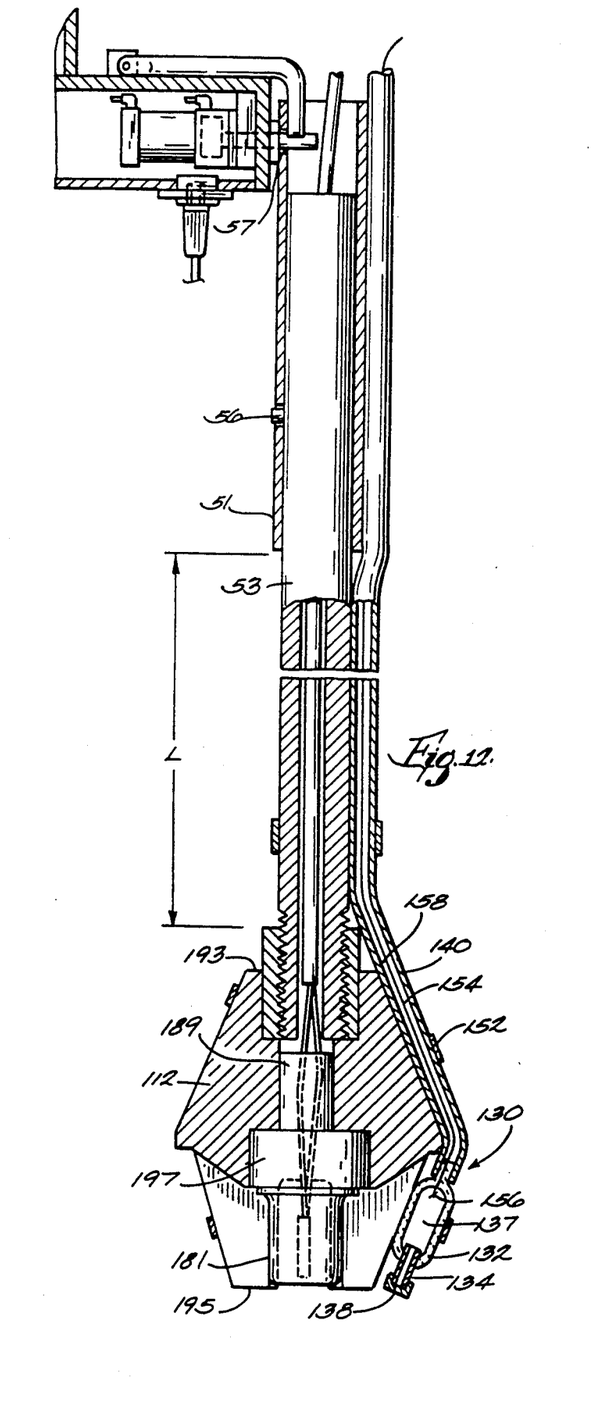
FIG. 12 is a side elevational view in fragmentary section of a modified embodiment of the probe.

FIG. 12 shows the probe of FIGS. 9, 10 and 11 with a sampler pod as disclosed in U.S. Pat. No. 4,881,824. The probe can be provided with an immersion sampler pod 130 which contains an outer protective coating of refractory fiber material as described above or other material as described in my U.S. Pat. No. 4,659,679 and can be provided with two spaced clam shell mold halves 132 with a fill tube 134 as shown in my U.S. Pat. No. 4,326,426. The entire disclosures of said patents are incorporated herein by reference. A small diameter paperboard vent tube 140 extends onto the sample body to communicate with the interior 137 of the mold to provide a vent for the sample cavity 137 to promote filling of the sampler when the probe is immersed. A fusible cap 138 on the fill tube 134 is typically employed to prevent entry of molten metal while the probe is lowered through the slag. The tube 140 extends up above the surface of the melt to ensure release of the air i the sample cavity as molten metal fills the cavity 137. The tube 140 can be connected to pipe 53.

The sample pod 130 can be releasably clamped to the weight 112 with a fusible clamp 152, such as a standard hose clamp. A find braided stainless steel wire 154 is located inside of the sampler between the two mold halves. A knot 156 anchors the wire 154 to the mold halves which are clamped together with a slight gap therebetween. The wire 154 extends through the interior 158 of the tube 140 to provide recovery of the sample mold 130. The molten steel fuses to wire and knot to provide a secure connection to the sampler.

The tube 140 can be made of a small diameter paperboard tube with an internal passage 158. A tube having a diameter three sixteenths of an inch can be formed or bent to conform somewhat to the shape of the handle or pipe 53. Paper tape can be used to releasably secure the tube to the pipe 53. The tube 140 also protects the wire 154. The tube 140 can be used with or without the wire to vent any sampler to a position above the molten metal. The vent tube 140 can be used with other immersion samplers such as that shown in U.S. Pat. No. 4,069,715, the entire disclosure of which is incorporated herein by reference. The vent tube 140 would be used instead of the vents 48 shown in FIG. 4 of that patent.

Figure 13:
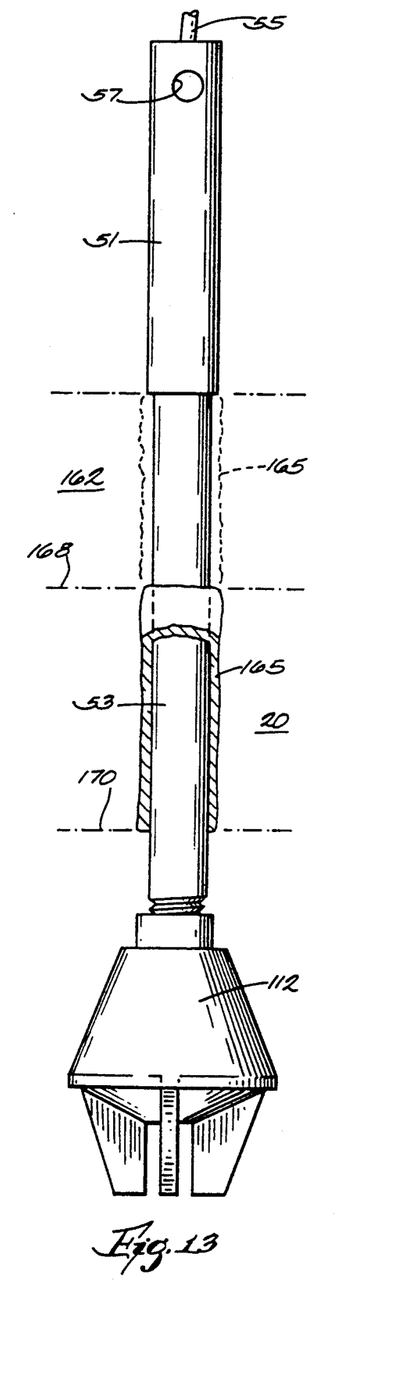
FIG. 13 is a side elevational view in fragmentary section showing immersion of the probe of FIG. 12 in a molten bath.

FIG. 13 is a view of the probe shown in FIG. 9 floating in molten steel 20 which has a layer of slag 162. It has been found that in use the steel pipe 53 between the paperboard sleeve or float tube 51 and the weight 112 acquires a steel skull 165. The skull 165 is formed on the pipe 53 when the probe is dropped into the steel by free fall. The weight of the probe causes the probe to momentarily penetrate the slag-steel interface 168 to a depth in the steel below level 170 which exposes the steel pipe 53 to the steel melt. Some steel forms an adhering layer or skull 165 shown in solid lines on the pipe 53 which remains adhered to the pipe 53 after the probe floats up the equilibrium position in FIG. 13 with the skull 165 in the latter position being shown in broken lines. The skull 165 may vary in thickness depending on conditions of the melt. One quarter inch wall thickness is typical for the skull 165. It is believed that the added weight from the skull 165 when the skull 165 is located in or above the less dense slag layer 162 assures proper positioning of the sensor and sampler in the steel below interface 168. Adequate penetration of the weight and sensor or sampler 130 into the steel with the probe remaining in vertical alignment prevents burn-through of the wires as described in U.S. Pat. No. 4,881,824. The skull 165 weight overcomes the buoyancy provided by some of the submersed cavities in the probe. Thus the length of exposed pipe between the float and weight is important both as a weight and as a carrier for the steel skull. A length L of exposed pipe of 24 inches or more has been found appropriate to provide a good heavy skull 165. The pipe described is thick walled such as one quarter inch wall thickness to provide added weight. The bomb 112 employed with this pipe was made from cast iron and had a length of 5 ⅛ inches maximum diameter of 3½ inches and a weight of 7 lbs. The central opening 181 was 1.685 inches wide or in diameter at its maximum width and 1 5/8 inches deep. Cavity 189 was 1⅛ inches in diameter. The surface 193 was 1.7 inches in diameter. Face 195 was 2 inches in diameter. Cavity 197 was ⅞ inches deep and 1.7 inches in diameter.

I claim:

1. In a probe and cable assembly wherein said probe is weighted and carries a sensor for measuring a characteristic of a molten metal bath, the improvement which comprises said probe being mounted vertically on a boom pivotable to a position over the bath, means carried by said boom which couple and decouple said probe from said boom, a cable storage container including means to mount said cable storage container on the boom, said storage container containing cable in a random packed condition of a sufficient length to enable the probe to reach a position in said molten metal bath for useable readings upon release and free fall immersion therein, said cable being attached at one end to said sensor and at the opposite end to an electrical circuit for monitoring signals from said sensor.

2. An improved probe and cable assembly according to claim 1 wherein said electrical circuit includes remote indicator means for indicating the operativeness of said sensor, and the fact of release of said sensor.

3. Apparatus according to claim 1 wherein said probe carries a sampler for taking a sample of a molten metal bath said sampler being attached to the probe by means of a 4. The apparatus of claim 1 wherein said means for coupling and decoupling said probe from said boom comprises a pin which is inserted in an aperture in said probe to couple the probe to the boom and which decouples and releases the probe to fall vertically into said bath when said pin is retracted.

5. Apparatus in accordance with claim 4 wherein said pin is actuated by an air cylinder to afford reciprocating recti-linear movement from an advanced position to a retracted position.

6. Apparatus in accordance with claim 4 wherein said probe comprises a paperboard sleeve and said aperture is formed in the side wall of the paperboard sleeve.

* * * * *

UNITED STATES PATENT AND TRADEMARK OFFICE
CERTIFICATE OF CORRECTION

PATENT NO. : 5,168,764

DATED : December 8, 1992

INVENTOR(S) : Richard A. Falk

It is certified that error appears in the above—identified patent and that said Letters Patent is hereby corrected as shown below:

Column 8, Claim 3, Line 6
               After "a" insert --- fusible clamp. ---

Signed and Sealed this

Twenty-sixth Day of October, 1993

Attest:

BRUCE LEHMAN

Attesting Officer     Commissioner of Patents and Trademarks